United States Patent
Cheng et al.

(10) Patent No.: US 10,376,888 B2
(45) Date of Patent: Aug. 13, 2019

(54) DEVICE FOR STORAGE AND DISPENSING OF REAGENTS

(71) Applicant: CENTRILLION TECHNOLOGY HOLDINGS CORPORATION, Grand Cayman (KY)

(72) Inventors: Jeremy Cheng, San Jose, CA (US); Wei Zhou, Saratoga, CA (US)

(73) Assignee: CENTRILLION TECHNOLOGY HOLDINGS CORPORATION, Grand Cayman (KY)

( * ) Notice: Subject to any disclaimer, the term of this patent is extended or adjusted under 35 U.S.C. 154(b) by 305 days.

(21) Appl. No.: 15/319,229

(22) PCT Filed: Jul. 1, 2015

(86) PCT No.: PCT/US2015/038777
§ 371 (c)(1),
(2) Date: Dec. 15, 2016

(87) PCT Pub. No.: WO2016/004171
PCT Pub. Date: Jan. 7, 2016

(65) Prior Publication Data
US 2017/0128944 A1 May 11, 2017

Related U.S. Application Data

(60) Provisional application No. 62/020,505, filed on Jul. 3, 2014, provisional application No. 62/062,300, filed on Oct. 10, 2014.

(51) Int. Cl.
*G01N 1/00* (2006.01)
*B01L 3/00* (2006.01)
(Continued)

(52) U.S. Cl.
CPC .............. *B01L 3/52* (2013.01); *B01L 3/523* (2013.01); *B01L 3/527* (2013.01); *G01N 21/85* (2013.01);
(Continued)

(58) Field of Classification Search
CPC ....................................................... G01N 1/00
See application file for complete search history.

(56) References Cited

U.S. PATENT DOCUMENTS 4,029,473 A 6/1977 Sharples
4,068,528 A 1/1978 Gundelfinger
(Continued)

FOREIGN PATENT DOCUMENTS

EP 0947819 A2 10/1999
WO WO-0141930 A1 6/2001
(Continued)

OTHER PUBLICATIONS

U.S. Appl. No. 15/200,408 Office Action dated Jun. 8, 2018.
(Continued)

*Primary Examiner* — Jyoti Nagpaul
(74) *Attorney, Agent, or Firm* — Wilson Sonsini Goodrich & Rosati

(57) ABSTRACT

A reagent storage and dispensing apparatus comprises a housing, storage wells disposed within an internal volume of the housing, and a valve. The housing comprises a shared outlet chamber. The wells can be selected to be in fluid communication with the shared outlet channel through individual outlet channels. The valve is coupled to the housing and is rotated to select a well to be in fluid communication with the shared outlet channel while preventing the remaining wells from being in fluid communication. As the valve is rotated, the wells and their individual outlet channels remain stationary. To dispense fluid from or draw fluid into
(Continued)

the selected well, positive or negative pressure, respectively, is introduced into the internal volume. Pressurization of the internal volume also pressurizes the plurality of wells, though the valve allows only fluid flow for the selected well.

20 Claims, 15 Drawing Sheets

(51) Int. Cl.
    *G01N 35/10*     (2006.01)
    *G01N 21/85*     (2006.01)
    *G01N 33/487*     (2006.01)

(52) U.S. Cl.
    CPC ....... *G01N 33/487* (2013.01); *G01N 35/1002* (2013.01); *B01L 3/502738* (2013.01); *B01L 2200/16* (2013.01); *B01L 2300/021* (2013.01); *B01L 2300/042* (2013.01); *B01L 2300/0803* (2013.01); *B01L 2300/0861* (2013.01); *B01L 2400/0487* (2013.01); *B01L 2400/0633* (2013.01); *B01L 2400/0644* (2013.01)

(56) References Cited

U.S. PATENT DOCUMENTS

| | | | |
|---|---|---|---|
| 4,822,569 | A | 4/1989 | Pellegrino |
| 4,889,069 | A | 12/1989 | Kawakami |
| 5,158,751 | A | 10/1992 | Del et al. |
| 5,310,523 | A | 5/1994 | Smethers et al. |
| 5,599,501 | A | 2/1997 | Carey et al. |
| 5,695,817 | A | 12/1997 | Tateyama et al. |
| 5,843,527 | A | 12/1998 | Sanada |
| 5,922,288 | A | 7/1999 | Herst |
| 6,162,602 | A | 12/2000 | Gautsch |
| 6,223,453 | B1 | 5/2001 | Matheson et al. |
| 6,247,479 | B1 | 6/2001 | Taniyama et al. |
| 6,379,242 | B1 | 4/2002 | Wiseman, Sr. et al. |
| 6,432,719 | B1 | 8/2002 | Vann et al. |
| 6,484,907 | B1 | 11/2002 | Evans |
| 6,644,364 | B1 | 11/2003 | Feygin |
| 6,660,233 | B1 | 12/2003 | Coassin et al. |
| 6,672,336 | B2 | 1/2004 | Nichols |
| 6,748,975 | B2 | 6/2004 | Hartshorne et al. |
| 6,786,224 | B2 | 9/2004 | Wong |
| 6,786,253 | B2 | 9/2004 | Feygin |
| 6,790,620 | B2 | 9/2004 | Bass et al. |
| 6,870,185 | B2 | 3/2005 | Roach et al. |
| 7,497,995 | B2 | 3/2009 | Johnson et al. |
| 7,618,590 | B2 | 11/2009 | Gleason et al. |
| 7,998,437 | B2 | 8/2011 | Berndt et al. |
| 8,008,080 | B2 | 8/2011 | Tokhtuev et al. |
| 8,097,225 | B2 | 1/2012 | Padmanabhan et al. |
| 8,178,352 | B2 | 5/2012 | Tokhtuev et al. |
| 8,241,013 | B2 | 8/2012 | Moeller et al. |
| 8,286,663 | B2 | 10/2012 | Kallback et al. |
| 8,287,954 | B2 | 10/2012 | Yoshihara et al. |
| 8,536,099 | B2 | 9/2013 | Oldham et al. |
| 8,727,178 | B1 | 5/2014 | Carter et al. |
| 8,956,694 | B2 | 2/2015 | Takeguchi et al. |
| 9,328,382 | B2 | 5/2016 | Drmanac et al. |
| 2003/0012697 | A1 | 1/2003 | Hahn et al. |
| 2004/0171166 | A1 | 9/2004 | Hunter |
| 2005/0232821 | A1 | 10/2005 | Carrillo et al. |
| 2005/0236051 | A1 | 10/2005 | McBeth et al. |
| 2005/0271814 | A1 | 12/2005 | Chang et al. |
| 2006/0002827 | A1 | 1/2006 | Curcio et al. |
| 2006/0057954 | A1 | 3/2006 | Hrebeniuk |
| 2009/0111168 | A1 | 4/2009 | Kim et al. |
| 2010/0028204 | A1 | 2/2010 | Lee et al. |
| 2010/0047047 | A1 | 2/2010 | Mayer et al. |
| 2010/0276617 | A1 | 11/2010 | Yasunaga |
| 2011/0088727 | A1 | 4/2011 | Slowe |
| 2012/0028811 | A1 | 2/2012 | Craighead et al. |
| 2014/0038854 | A1 | 2/2014 | Roth et al. |
| 2014/0186940 | A1 | 7/2014 | Goel |
| 2015/0343484 | A1 | 12/2015 | Kukas |
| 2016/0046985 | A1 | 2/2016 | Drmanac et al. |
| 2016/0168632 | A1 | 6/2016 | Edwards |
| 2017/0001165 | A1 | 1/2017 | Crnogorac et al. |
| 2017/0022554 | A1 | 1/2017 | Drmanac et al. |

FOREIGN PATENT DOCUMENTS

| | | |
|---|---|---|
| WO | WO-2008022332 A2 | 2/2008 |
| WO | WO-2009034181 A2 | 3/2009 |
| WO | WO-2012106546 A2 | 8/2012 |
| WO | WO-2012106546 A3 | 11/2013 |
| WO | WO-2015017759 A1 | 2/2015 |
| WO | WO-2016004171 A1 | 1/2016 |
| WO | WO-2017004502 A1 | 1/2017 |

OTHER PUBLICATIONS

EP16177654.7 Office Action dated Jul. 16, 2018.
Office Action dated Nov. 2, 2017 for U.S. Appl. No. 15/200,408.
PCT/US2016/040661 International Preliminary Report on Patentability dated Jan. 2, 2018.
PCT/US2015/038777 International Preliminary Report on Patentability dated Jan. 3, 2017.
Ausubel, et al., Current protocols in molecular biology. John Wiley &Sons. 1987.
Birren, et al., Genome analysis: a laboratory manual, Cold spring harbor laboratory press. 1999.
Eckstein, F., Oligonucleotides and analogues: a practical approach, IRL 1991.
European search report with written opinion dated Nov. 15, 2016 for EP16177654.7.
Gait, MJ., Oligonucleotide Synthesis: A Practical approach, IRL Press. 1984.
International Search Report and Written Opinion dated Sep. 16, 2016 for International Application PCT/US2016/040661.
International search report with written opinion dated Dec. 3, 2015 for PCT/US2015/038777.
Maniatis, et al., Molecular Cloning: A Laboratory Manual. Cold Spring Harbor Laboratory Press; 1982.
Ogilvie, et al. Solvent Processing of PMMA and COC Chips for Bonding Device with Optical Quality Surfaces. 14th International Conference on Miniaturized Systems for Chemistry and Life Sciences, Oct. 3-7, 2010, Groningen, The Netherlands.
Sambrook, et al., Molecular Cloning: A Laboratory Manual. 2nd edition. Cold spring harbor laboratory press. 1989.

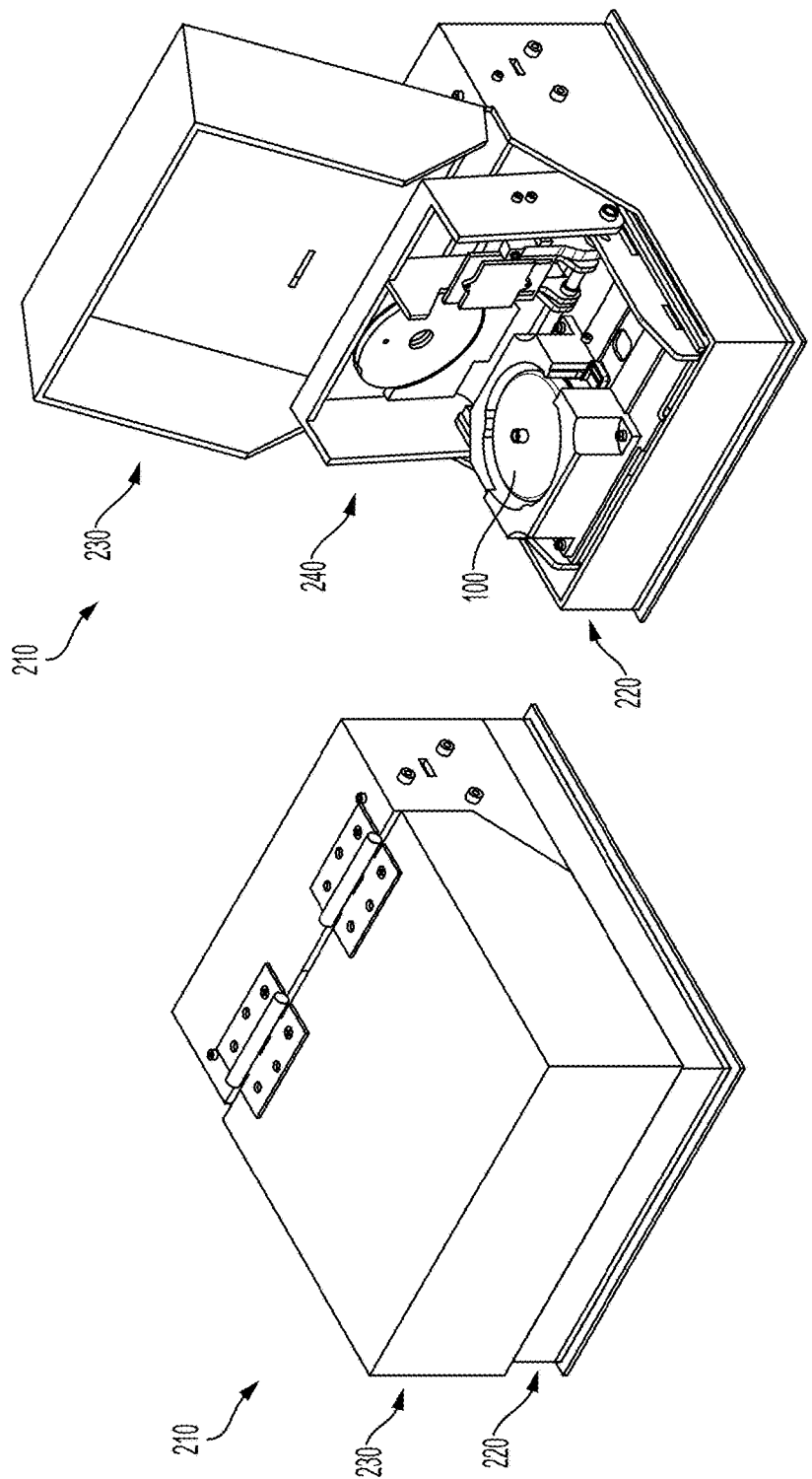

DEVICE FOR STORAGE AND DISPENSING OF REAGENTS

CROSS-REFERENCE

This application claims the benefit of U.S. Provisional Application No. 62/020,505 filed on Jul. 3, 2014, and U.S. Provisional Application No. 62/062,300 filed on Oct. 10, 2014, each of which application is incorporated herein by reference in its entirety.

BACKGROUND

Many experimental or diagnostic procedures in the chemical, biological, and biochemical arts require the use of samples or reagents. Samples and reagents often need to be stored and dispensed in a standard, predicable, and reliable manner, especially for many automated assay systems. Storage and dispensing devices used in such automated systems, however, are less than ideal in many circumstances. Many currently available storage and dispensing devices can be difficult to manufacture and may have reliability issues that necessitate frequent repair. Accordingly, such devices may be expensive to purchase and maintain. In many cases, such devices are prohibitively expensively for many diagnostic or other applications. These applications may include the rapid, low-cost sequencing of an individual's whole or partial genome and the rapid and reliable detection of infectious diseases or biological agents (for example, Anthrax and the like). There are therefore needs for low-cost, reliable reagent storage and dispensing devices and systems that address at least some of the above challenges.

SUMMARY

Reliable, low-cost reagent/sample storage and dispensing devices are described herein. These storage and dispensing devices may be suitable for use with low-cost and compact sequencing platforms (for example, for polynucleotides, polypeptides, etc.). The storage and dispensing devices described herein may comprise a plurality of reagent wells which may be selected for dispensing of individual reagents or solutions from individual wells. An outlet channel may be provided to couple the device to a flow cell to be analyzed with the sequencing platform. The selection of individual wells for dispensing of the contents therein may be achieved with a valve which may be actuated by the sequencing platform. The valve may be actuated at least thousands of times (for example, 4,000 to 8,000) before mechanical failure starts to become a likely concern. The valve may be actuated without the need to move any of the reagent wells or dispenser channels extending therefrom. The reagent wells and dispensing channels may remain stationary while a specific reagent well is selected for dispensing, reducing the risk for mechanical failure. The storage and dispensing devices described herein may be operational through a variety of temperature ranges such as the temperature of cold storage (for example, below the freezing temperature of water at atmospheric pressure) and the high heat during sequencing operations (for example, 85° C.). The storage and dispensing devices described herein can therefore be highly robust. At the same time, the storage and dispensing device may be interchangeable within the sequencing platform such that the storage and dispensing devices are disposable and easily replaced such as when mechanical failure of the valve or other mechanical element of the storage and dispensing device occurs. The storage and dispensing devices described herein may be manufactured in a low-cost, rapid manner in many ways, such as by one or more of injection molding, 3D printing, 2D laser cutting, CNC milling, extrusion, solvent bonding, or the like.

Aspects of the present disclosure provide an apparatus for the storage and dispensing of one or more reagents or fluids. The apparatus may comprise housing which may be formed by a base assembly and a cover coupled together, a plurality of reagent storage wells, and a valve. The housing or base assembly may comprise an outlet channel. The housing may define an internal volume which may be between the cover and the base assembly. The housing or cover may comprise an inlet port configured to the internal volume to be pressurized (that is, allow pressure to be introduced into the internal volume). The plurality of reagent storage wells may be coupled to the base assembly and may be disposed within the internal volume. The plurality of reagent storage wells may be selectively in fluid communication with the outlet channel. The valve may be coupled to the housing or base assembly. The valve may be rotated to select an individual reagent storage well to be in fluid communication with the outlet channel while preventing at least one other reagent storage well, typically all of the remaining reagent storage wells, from being in fluid communication with the outlet channel. Pressurizing the internal volume or introducing pressure into the internal volume through the inlet may cause fluid to be drawn into or egress from the selected individual reagent storage well.

The valve, for example, may have a first configuration and a second configuration. The first configuration may allow a first reagent storage well of the plurality of reagent storage wells to be in fluid communication with the outlet channel and may prevent or restrict a second reagent storage well of the plurality of reagent storage wells from being in fluid communication with the outlet channel. The second configuration may allow the second reagent storage well to be in fluid communication with the outlet channel and may prevent or restrict the first reagent storage well from being in fluid communication with the outlet channel. Further configurations for further reagent storage wells are also contemplated.

The introduced pressure may comprise one or more of negative pressure or positive pressure. The introduction of positive pressure into the internal volume may cause a reagent or fluid stored in the selected individual reagent storage well of the plurality of reagent storage wells to egress through the outlet channel. The introduction of negative pressure into the internal volume may cause a reagent or fluid present in the outlet channel to retreat or be drawn into the selected reagent storage well of the plurality of reagent storage wells. The positive or negative pressure may be introduced by the introduction or removal of a metered or pre-determined volume of fluid such as air, water, saline, buffer, or the like into or out of the internal volume, leading to an inflow or outflow of fluid from a selected well at the same or substantially the same metered or pre-determined volume. The one or more reagent storage wells of the plurality of reagent storage wells may comprise an open port to balance pressure between the internal volume and a storage volume of the one or more reagent storage wells. While each reagent storage well may be pressurized through their open ports from the pressurization of the internal volume of the housing, only the selected storage well is open for fluid communication such that the pressurization causes the fluid therewithin to egress (or alternatively cause a fluid to be drawn into the selected storage well). Each of the reagent storage wells may be pressurized uniformly from being open to the internal volume of the housing.

The base assembly may comprise a base coupled to the plurality of reagent storage wells and a cap coupled to the base. One or more of the cap or the base may comprise a plurality of fluid transfer channels open to the plurality of reagent storage wells. The plurality of fluid transfer channels may be coupled to the valve to allow the plurality of reagent storage wells to selectively be in fluid communication with the outlet channel. One or more of the cap or the base may comprise an outlet manifold in fluid communication with the outlet channel. The valve may comprise a valve channel for allowing fluid communication between the outlet manifold and a selected fluid transfer channel of the plurality of fluid transfer channels. The portion of the valve may be configured to be actuated to place the valve channel in fluid communication between the outlet manifold and the selected fluid transfer channel. When the individual storage well is selected, the valve may be in fluid communication between the outlet manifold and a fluid transfer channel in fluid communication with the selected individual reagent storage well. The valve may be rotated to deselect the individual reagent storage well such that the valve channel is no longer in fluid communication between the outlet manifold and the fluid transfer channel in fluid communication with the deselected individual reagent storage well. The valve in the first configuration may have the valve channel in fluid communication between the outlet manifold and a first fluid transfer channel in fluid communication with the first reagent storage well. The valve in the second configuration may have the valve channel in fluid communication between the outlet manifold and a second fluid transfer channel in fluid communication with the second reagent storage well.

The base assembly may have a central portion and the valve may be coupled to the base assembly at the central portion. The base assembly may have an outer diameter and the outlet channel may comprise an outlet port at or beyond the outer diameter. The base assembly may comprise a protrusion beyond the outer diameter and the outlet port is disposed at the protrusion. The plurality of reagent storage wells may be disposed about the central portion of the base assembly.

The valve may be configured to be switched from the first configuration to the second configuration while the plurality of reagent storage wells and the outlet channel remain stationary. When the valve is rotated to select the individual reagent storage well, the plurality of reagent storage wells and the outlet channel may remain stationary.

Aspects of the present disclosure also provide a system for imaging a flow cell. The system comprises the reagent or fluid storage and dispensing apparatus described herein, a flow cell, an imaging source, a pressure source, a waste storage chamber, and an actuator. The flow cell may be coupled to the outlet channel of the reagent or fluid storage and dispensing apparatus. The imaging source may be coupled to the flow cell to image the flow cell. The pressure source may be coupled to an inlet port of the cover to provide pressure to the internal chamber. The waste storage chamber may be coupled to the flow cell. The actuator may be configured to actuate the valve to move the valve between the first and second configurations. The actuator may be configured to rotate the valve to select the individual storage well of the storage and dispensing apparatus.

Aspects of the present disclosure also provide a method for dispensing one or more reagents. A reagent storage chamber may be provided. A valve of the reagent storage chamber may be actuated to select a first reagent or fluid for dispensing. The first reagent or fluid may be stored in a first reagent storage well of the reagent storage chamber. To select the first reagent or fluid for dispensing, a valve channel of the valve may be aligned with a first transfer channel of the first reagent storage well with an outlet manifold of the reagent storage chamber to allow fluid communication therebetween. The internal volume of the reagent storage chamber may be pressurized (that is, pressure may be introduced into the internal volume of the reagent storage chamber) to pressurize or introduce the pressure into a storage volume of the first reagent storage well, thereby causing the first reagent or fluid to egress from the first reagent storage chamber and through the first transfer channel, valve channel, and outlet manifold. The valve may be actuated to select a second reagent or fluid for dispensing. The second reagent may be stored in a second reagent storage well of the reagent storage chamber. Selecting the second reagent or fluid for dispensing may position the valve channel out of alignment with the first transfer channel and the outlet manifold such that the first reagent or fluid is prevented from being dispensed from the first reagent storage well. Each reagent well may be pressurized uniformly from the pressure in the internal volume, but fluid may only be dispensed from the selected reagent well which is in fluid communication with the shared outlet manifold and shared outlet channel.

Selecting the second reagent or fluid for dispensing may align the valve channel with a second transfer channel of the second reagent storage well with the outlet manifold to allow fluid communication therebetween. Pressure may be introduced into the internal volume of the reagent storage chamber to introduce the pressure into a storage volume of the second reagent well, thereby causing the second reagent or fluid to egress from the second reagent storage chamber and through the second transfer channel, valve channel, and outlet manifold. Pressurizing the internal volume pressurizes storage volumes of a plurality of storage wells of the reagent storage chamber. Pressurizing the plurality of storage wells may cause only the first fluid to egress from the first storage well while fluid in the remaining storage wells does not egress therefrom. The positive or negative pressure may be introduced by the introduction or removal of a metered or pre-determined volume of fluid such as air, water, saline, buffer, or the like into or out of the internal volume, leading to an inflow or outflow of fluid from a selected well at the same or substantially the same metered or pre-determined volume.

Actuating the valve to select the first reagent or fluid for dispensing or actuating the valve to select the second reagent or fluid for dispensing may comprise rotating at least a portion of the valve relative to the housing or a base assembly of the reagent storage chamber.

Pressure may be introduced into the internal volume by introducing a fluid into the internal volume.

The first and second reagent storage wells may remain stationary while the valve is actuated to select the first or second reagent or fluid for dispensing.

Aspects of the present disclosure also provide a method for aspirating a fluid. A fluid storage chamber coupled to a fluid source may be provided. A valve of the fluid storage chamber may be actuated to select a first fluid storage well of the fluid storage chamber for fluid aspiration. The first fluid storage well may be selected by aligning a valve channel of the valve with a first transfer channel of the first fluid storage well with a manifold of the fluid storage chamber to allow fluid communication therebetween. Negative pressure or suction may be introduced into an internal volume of the fluid storage chamber to introduce the negative pressure or suction into a storage volume of the first fluid storage well, thereby causing a fluid from the fluid source to flow from the fluid source and through the manifold and the first fluid transfer channel into the fluid storage well of the first fluid storage well. The positive or negative pressure may be introduced by the introduction or removal of a metered or pre-determined volume of fluid such as air, water, saline, buffer, or the like into or out of the internal volume, leading to an inflow of fluid from a selected well at the same or substantially the same metered or pre-determined volume. The valve may be actuated to select a fluid storage well of the fluid storage chamber for fluid aspiration. Selecting the second fluid storage well may position the valve channel out of alignment with the first transfer channel and the manifold such that fluid from the fluid source is prevented from being aspirated into the first fluid storage well. Thus, while negative pressure may be applied to each reagent well, fluid may only be drawn into the selected reagent well which is in fluid communication with the shared manifold and shared main channel (which may still be referred to as the outlet channel herein).

Selecting the second fluid storage well for fluid aspiration may align the valve channel with a second transfer channel of the second fluid storage well with the manifold to allow fluid communication therebetween. Negative pressure or suction may be introduced or applied into the internal volume of the fluid storage chamber to introduce the negative pressure or suction into the storage volume of the second fluid storage well, thereby causing the fluid from the fluid source to flow from the fluid source and flow through the manifold and the second fluid transfer channel into the second fluid storage well. The positive or negative pressure may be introduced by the introduction or removal of a metered or pre-determined volume of fluid such as air, water, saline, buffer, or the like into or out of the internal volume, leading to an inflow of fluid from a selected well at the same or substantially the same metered or pre-determined volume.

Actuating the valve to select the first fluid storage well or actuating the valve to select the second fluid storage well may comprise rotating at least a portion of the valve relative to a base assembly of the fluid storage chamber.

Negative pressure or suction may be introduced into the internal volume by aspirating a fluid from the internal volume.

The first and second fluid storage wells may remain stationary while the valve is actuated to select the first or second fluid storage wells.

The fluid source may comprise a flow cell coupled to the fluid storage chamber.

Introducing negative pressure or suction into the internal volume may introduce the negative pressure or suction into storage volumes of a plurality of storage wells of the storage chamber. The negative pressure or suction may be introduced into the storage volumes uniformly. The negative pressure or suction introduced may cause the fluid to be drawn only into the first storage well while the fluid is prevented from being drawn into the remaining storage wells. The selected first storage well may be a storage well designated for waste.

Aspects of the present disclosure also provide a method for performing three or more sequential reactions. A dispenser unit may be provided. The dispenser unit may be coupled to a flow cell. The flow cell may be configured to carry out the sequential reactions. A plurality of reagents may be sequentially dispensed from the dispenser unit to the flow cell to carry out the sequential reactions. Each reagent of the plurality of reagents may be dispensed as a discrete volume. Each reagent may be selected for dispensing while each well of a plurality of reagent wells of the dispenser unit remains stationary and unselected reagents are prevented from being dispensed. A fluid may also be aspirated from the flow cell into the single dispenser unit. To sequentially dispense the plurality of reagents from the dispenser unit, an internal volume of the dispenser unit may be pressurized to pressurize the storage volumes of the reagent storage wells (that is pressure or suction may be introduced into the internal volume), thereby causing fluid within only the storage volume of a selected storage well to be dispensed from the dispenser unit while fluid egress from the unselected storage wells is prevented or restricted.

Aspects of the present disclosure also provide a method for performing three or more sequential reactions. Reagents are sequentially introduced from a dispenser unit to a flow cell to carry out the sequential reactions. The dispenser unit may be configured for dispensing the reagents as discrete volumes while reagent storage wells and an outlet channel of the dispenser unit remain stationary, thereby minimizing mechanical wear of the dispenser unit. To sequential introduce reagents from the dispenser unit, pressure or suction may be introduced into an internal volume of the dispenser unit to introduce the pressure or suction into the storage volumes of the reagent storage wells, thereby causing fluid within only the storage volume of a selected storage well to be dispensed from the dispenser unit while fluid egress from the unselected storage wells is prevented or restricted.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A shows a perspective view of a diagnostic platform (in a closed configuration) usable with the reagent storage and dispensing device of FIG. 1A, in accordance with many embodiments;

FIG. 2B shows a perspective view of the diagnostic platform (in an open configuration) of FIG. 2A;

FIG. 2I shows an exploded view of the bottom portion of the diagnostic mechanism of the diagnostic platform of FIG. 2A with the base and cover removed;

DETAILED DESCRIPTION

Reliable, low-cost, and robust reagent or fluid storage and dispensing devices as well as systems and method for their use are described herein. FIGS. 1A-1G show a reagent or fluid storage and dispensing device 100 and its component parts, in accordance with many embodiments.

Figure 1A:
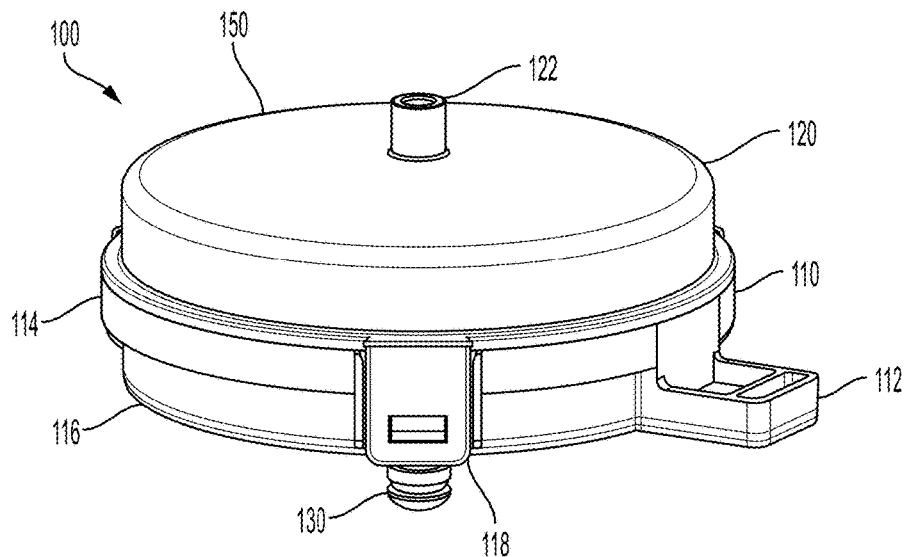
FIG. 1A shows a top perspective view of a reagent storage and dispensing device, in accordance with many embodiments.
Figure 1B:
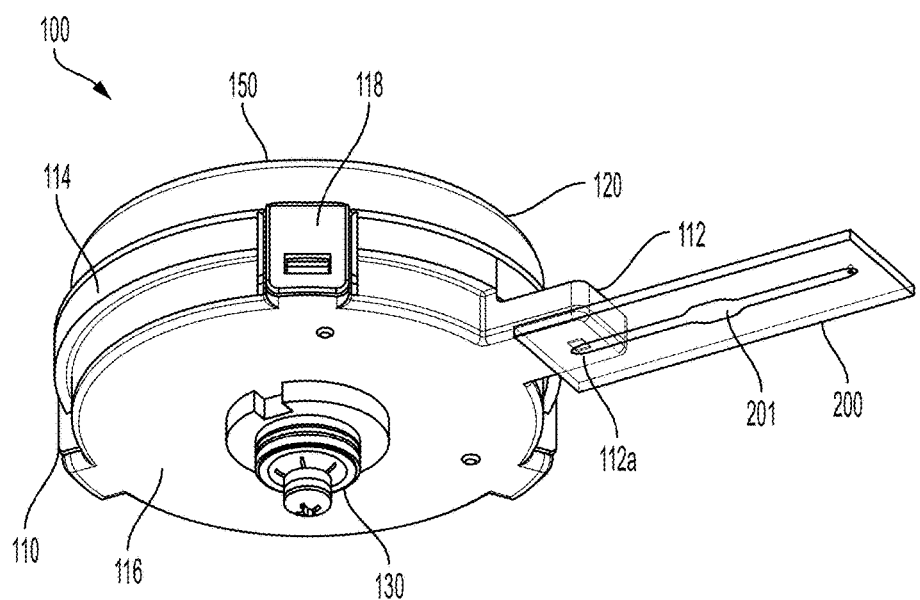
FIG. 1B shows a bottom perspective view of the reagent storage and dispensing device of FIG. 1A coupled to a flow cell.

FIG. 1A shows a top perspective view of the reagent storage and dispensing device 100. FIG. 1B shows a bottom perspective view of the device 100 coupled to a reaction tube or flow cell 200. Fluid(s), reagent(s), and/or sample(s) may be selectively dispensed in a desired sequence from the device 100 to the flow channel 201 of the flow cell 200. In the flow cell 200, various reactions (for example, sequencing and/or synthesis reactions) may occur in response to the introduced reagent(s) and/or sample(s). As these reactions occur, the flow cell 200 may be imaged as further described below. Multiple flow cells 200 may be used with a single device 100 and vice versa.

The reagent storage and dispensing device 100 may comprise a base assembly 110, a cover 120 coupled to the top of the base assembly 110 with mechanical couplings 118 to form a housing 150, and a valve assembly 130 coupled to the bottom of the base assembly 110. The base assembly 110 may comprise a outlet 112 which protrudes from the main circular body of the base assembly 110 to be coupled with the flow cell 200 as shown in FIG. 2A. An integral gasket may be provided with the outlet 112 to connect with the flow cell 200 and minimize contamination between experiments as well as to simplify maintenance. The base assembly 110 may comprise a base 114 and a cap 116 coupled to the bottom of the base 114. The base 114 and the cap 116 may be coupled to one another using an adhesive, vapor bonding (for example, as described by Ogilvie et al, "Solvent Processing of PMMA and COC Chips for Bonding Device with Optical Quality Surfaces," 14th International Conference on Miniaturized Systems for Chemistry and Life Sciences, 3-7 Oct. 2010, Groningen, The Netherlands), or the like. For example, the base 114 and the cap 116 may both be made of acrylic and may be vapor bonded to one another. The base 114 may have one or more concavities or elongate cut-outs on its bottom as further described below. When covered by the cap 116, the concavities or cutouts along with the cap 116 may define one or more fluid channels such as the outlet channel 112a which may be coupled to the flow cell channel 201 and/or the channels 148 further described below. Vapor bonding of the base 114 and the cap 116 may preserve these fluid channels as the base 114 and the cap 116 are bonded together in contrast with other bonding techniques such as the use of an adhesive or solvent bonding. The cover 120 may comprise a port 122 through which fluid such as pressurized gas may be introduced or removed. Introduction of fluid through the port 122 may urge one or more fluids, reagents, or samples out of the device 100. The valve assembly 130 may be actuated to select which fluid, reagent, or sample to be dispensed. As the valve assembly 130 is actuated, the base assembly 110 and the cover 120 may remain stationary such that movement of the device 100 when in use is minimized and the risk of mechanical failure is reduced.

Figure 1C:
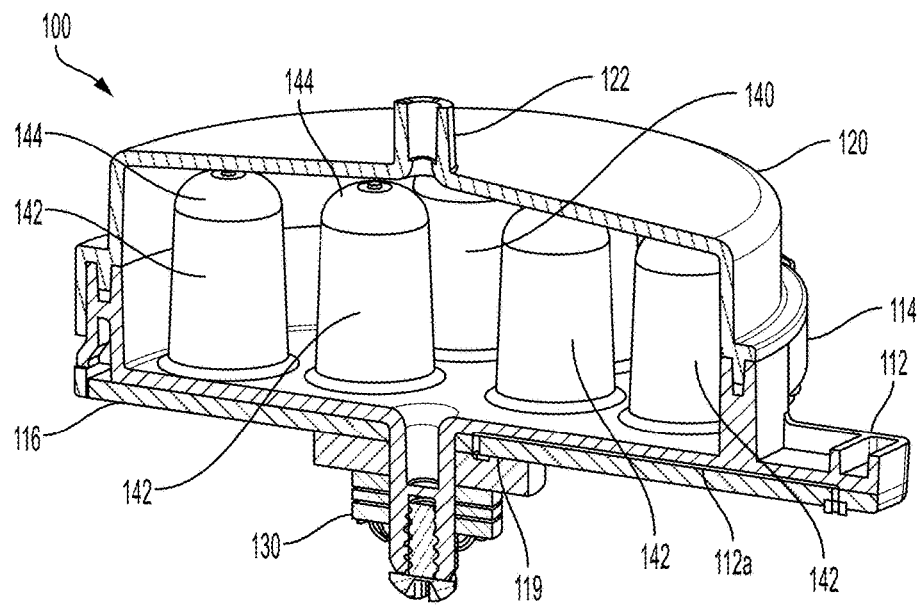
FIG. 1C shows a sectional view of the reagent storage and dispensing device of FIG. 1A.
Figure 1D:
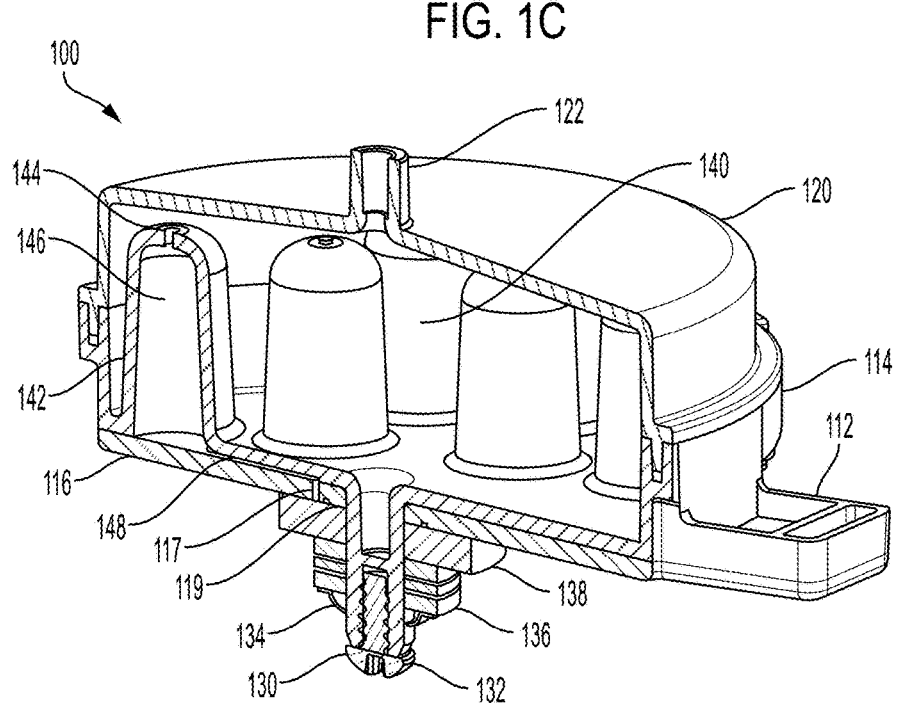
FIG. 1D shows a sectional view of the reagent storage and dispensing device of FIG. 1A.

FIGS. 1C and 1D show sectional views of the reagent storage and dispensing device 100. The coupling of the cover 120 and the base assembly 110 may define an internal volume 140. The internal volume 140 may be in fluid communication with the exterior environment through the port 122. Within the internal volume 140, the device 100 may comprise a plurality of storage wells 142 coupled to the base 114. The storage wells 142 may be arranged about a center of the base 114 or valve assembly 130, for example, in the manner of a carousel, albeit the storage wells 142 may be stationary relative to a movable portion of the valve assembly 130 as described further herein. There may be any number of storage wells 142 and a typical number may be 4-16. The storage wells 142 may be open at the bottom of the base 114 and may be sealed with the top side of the cap 116. The storage wells 142 may each have an internal storage volume 146 for storing reagent(s) and/or sample(s). A reagent or other fluids may be pre-packaged into the internal storage volumes 146. The internal storage volume 146 may have a variety of sizes. For example, the internal storage volume 146 may have a volume of 0.5 to 10 mL, 0.5 to 6 mL, 2 to 5 mL, etc. A typical volume for the internal storage volume 146 may be 2 mL. The storage wells 142 may further comprise a top port 144 in fluid communication with the internal volume 140 of the device 100. Reagent and/or sample may be introduced into the internal storage volumes 146 through these top ports 144. The reagent wells 142 may be sterilized chemically, thermally, or with variation as needed with the reagent(s) to be stored. The reagent wells 142 may be surface treated to improve sample recovery, for example, to reduce adsorption of biological samples to the well surface such as by siliconization of the well surfaces as used in Eppendorf LoBind Tubes and Plates available from Fisher Scientific International, Inc. of Hampton, N.H. Each reagent well 142 may remain stationary while the valve assembly 130 is actuated to select a reagent for dispensing and while the selected reagent(s) is dispensed.

The base assembly 110 may have a plurality of channels 148 defined between the base 114 and the cap 116 and each in fluid communication with the internal storage volume 146 of each storage well 142 (as shown in FIG. 1D.) When pressure is introduced into the internal volume 140 of the device 100 (such as by the introduction of fluid, air, water, saline, buffer, or the like through the port 122), the introduced pressure can be exerted through the ports 144 of the storage well 142. If a storage well 142 is selected for dispensing, the channel 148 of that storage well may be in fluid communication with the outlet channel 112a through the dispensing piece 138 of the valve assembly 130 such that the contents of the selected storage well may be dispensed. At least some of the contents of selected well 142 may advance from the storage volume 146, through the channel 148, through an individual outlet port 117 of the cap 116, through a channel 138c of the dispensing piece 138, through an outlet manifold 119 of the cap 116, and finally through the outlet channel 112a of the base assembly 110. The remaining storage wells 142 may be pressurized at the same time but without dispensing of their contents. The base cap 116 and/or the components of the valve assembly 130 (that is, the screw 132, the push nut 134, the thrust bearing 136, (which attach the dispensing piece 138 to the base assembly 110 with a sealing force) and the dispensing piece 138) may have external markers or indicia to indicate which of the wells 142 is selected for dispensing. Alternatively or in combination, one or more of the base assembly 110, the cover 120, or the valve assembly 130 may be at least partially transparent such that the selection of an individual well for reagent or sample dispensing can be clearly visualized. Furthermore, the introduction of negative pressure into the internal volume 140 (such as by the removal of fluid, air, buffer, or the like through the port 122) may cause the contents of the outlet channel 112a and/or the flow cell channel 201 to be withdrawn. That is, the reagent storage and dispensing device 100 may have two modes of use. In the first mode of use, positive pressure may be introduced into the internal volume 140 to cause a selected reagent to be dispensed from a selected reagent well 142. A metered, pre-determined volume of fluid (for example, air, water, buffer, saline, or the like) may be introduced to cause a same or substantially the same metered, pre-determined volume of the reagent to egress from the selected reagent well 142. In the second mode of use, negative pressure may be introduced into the internal volume 140 to cause fluid in the outlet channel 112a and/or the flow cell channel 201 to be withdrawn. Again, the volume of the fluid suctioned from the internal volume 140 may be the same or substantially the same as the volume of the fluid withdrawn. This fluid may be withdrawn into a selected reagent well 142 designated for waste. In the first mode of use, the actual volume of fluid dispensed may be within 10-20% of the volume desired and selected to be dispensed. The fluid may be dispensed with many flow rates. The fluid may be dispensed with a flow rate of 1 to 4 µl/s, for example. In many embodiments, the reagents dispensed are to be used for sequential reactions that may be reagent concentration dependent rather than volume or flow rate dependent. In the second mode of use, the actual volume of fluid withdrawn may be within 1-2 µL of the volume desired and selected to be withdrawn.

Figure 1E:
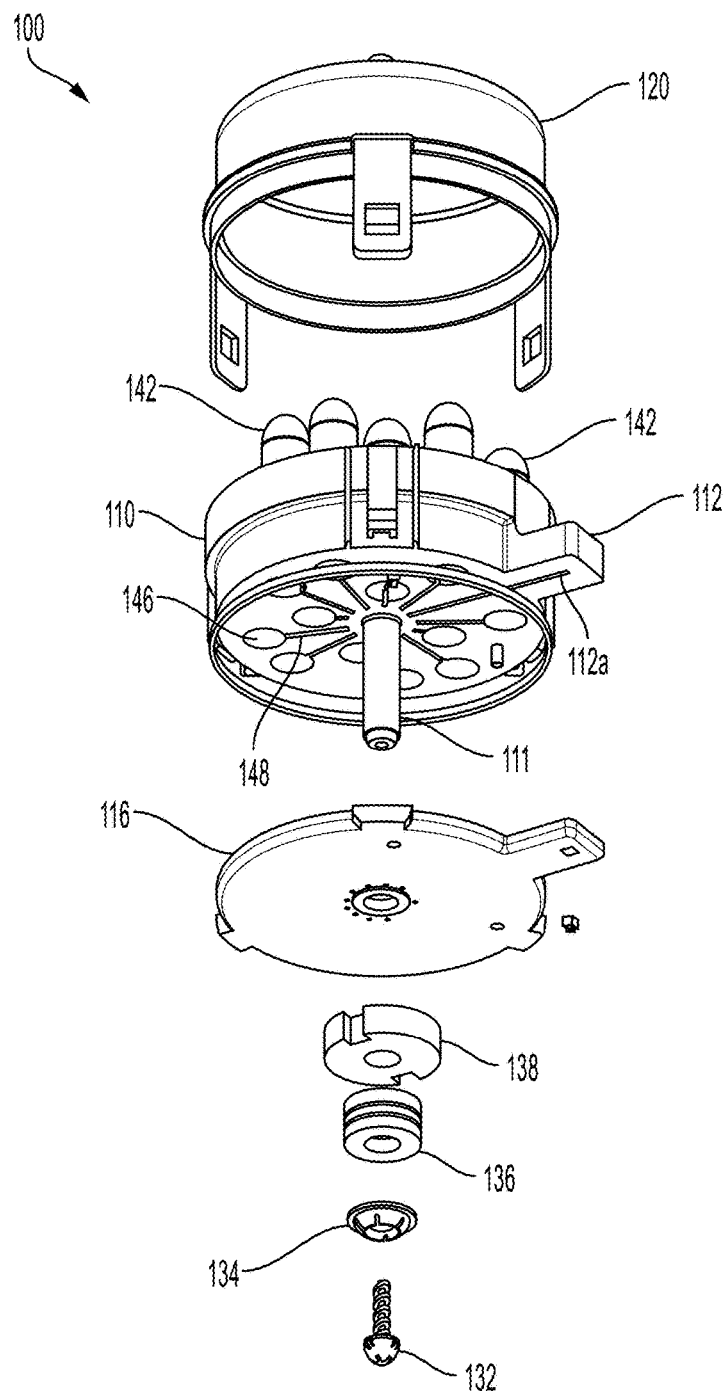
FIG. 1E shows an exploded view of the reagent storage and dispensing device of FIG. 1A.
Figure 1F:
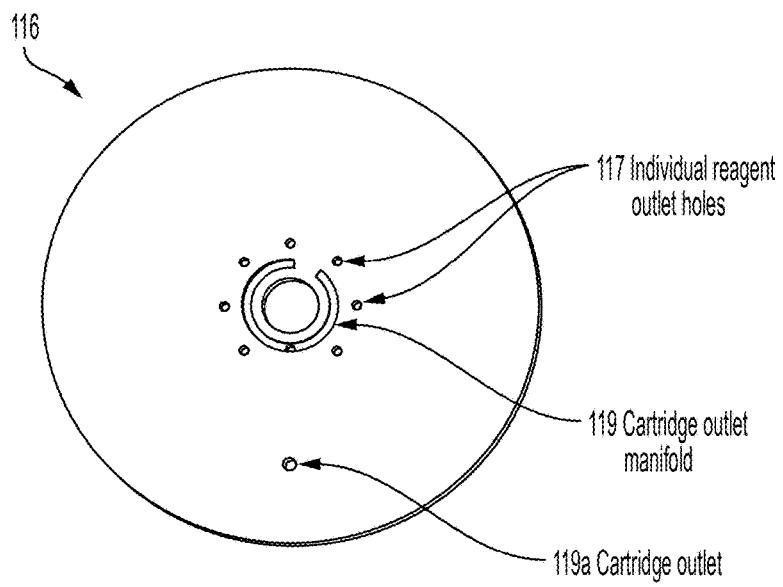
FIG. 1F shows a top perspective view of the base assembly cap of the reagent storage and dispensing device of FIG. 1A.
Figure 1G:
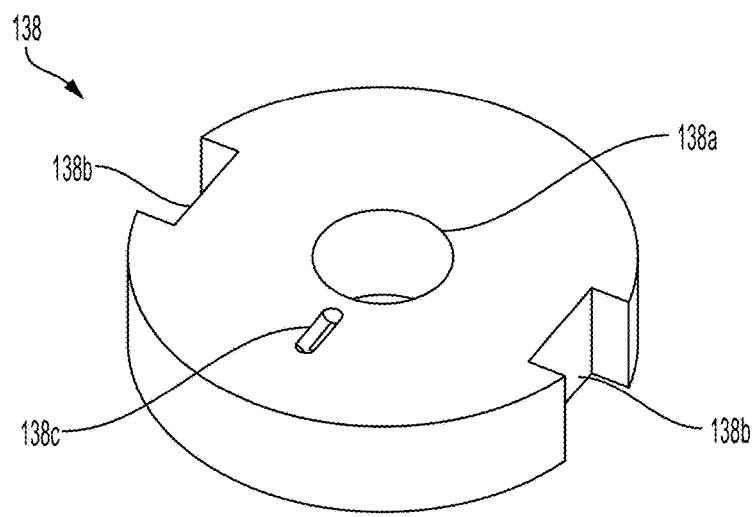
FIG. 1G shows a perspective view of the dispensing piece of the valve assembly of the reagent storage and dispensing device of FIG. 1A.

An exploded view of the reagent storage and dispensing device 100 is shown in FIG. 1E. As shown in FIG. 1E, the storage wells 142 may be arranged concentrically about a central portion of the base assembly 110, for example, the post 111. The internal storage volume 146 of each storage well 142 may be open to individual channels 148 which lead toward the central portion. The base assembly cap 116 may cover the bottom side of the base 114. As shown in FIG. 1F, the cap 116 may comprise individual outlet holes 117 for each storage well. The cap 116 may further comprise an outlet manifold 119. As shown in FIG. 1G, the valve dispensing piece 138 may comprise a channel 138c. When an individual storage well 142 is selected for dispensing, the channel 138c is moved into a position such that the outlet hole 117 of the selected storage well 142 is aligned with and in fluid communication with the outlet manifold 119 through the channel 138c. The outlet manifold 119 may be in fluid communication with the outlet channel 112a and the outlet 119a of the cap 116. When selecting an individual storage well 142 for reagent and/or sample dispensing, the dispensing piece 138 is typically only rotated while the remaining components of the device 100 remain stationary. This reduced movement of parts can provide for improved longevity of the device 100 as it undergoes repeated use (that is, selection and dispensing). As shown in FIG. 1G, the dispensing piece 138 may comprise one or more brackets 138b to facilitate the coupling of the dispensing piece 138 to an automated actuator. The dispensing piece 138 may be rotated about the aperture 138a through which the screw 132 may be threaded. The dispensing piece 138 may be made of polypropylene. The rotation of the dispensing piece 138 may be facilitated by the thrust bearing 136 which may comprise a nylon/steel ball. The valve assembly 130 may also be removed from the base assembly 110 such that the valve assembly 130 is easily replaceable. As switching from a first reagent well 142 to a second reagent well 142 typically requires only a rotation of the dispensing piece 138, the time interval between dispensing of a first reagent and a second reagent can be very short, for example, in the range of 100-200 ms. In this manner, multiple reagents may be sequentially introduced to the flow cell 200 for sequential reactions that can occur in short period of time, for example, 200 ms to 10 s.

The reagent storage and dispensing device 100 may be used with a diagnostic platform 210 as shown in FIGS. 2A-2I. Multiple reagent storage and dispensing device 100 may be used with a single diagnostic platform 210, which may be reusable, and vice versa. For example, a first reagent storage and dispensing device 100 may be used with a diagnostic platform 210 to perform a series of reactions for a first sample. Afterwards, the first device 100 may be replaced with a second device 100 to perform a series of reactions for a second sample using the same diagnostic platform. Different flow cells 200 may be provided for the first and second samples. One or more of the reagent storage dispensing device 100 or the flow cell 200 may be disposable after use.

The diagnostic platform 210 may comprise an outer shell or body 220 and a cover 230 pivotably coupled to the body 220, as shown in FIGS. 2A (closed configuration) and 2B (open configuration). The outer shell or body 220 and the cover 230 may house the diagnostic mechanism 240 as shown in FIG. 2B.

Figure 2C:
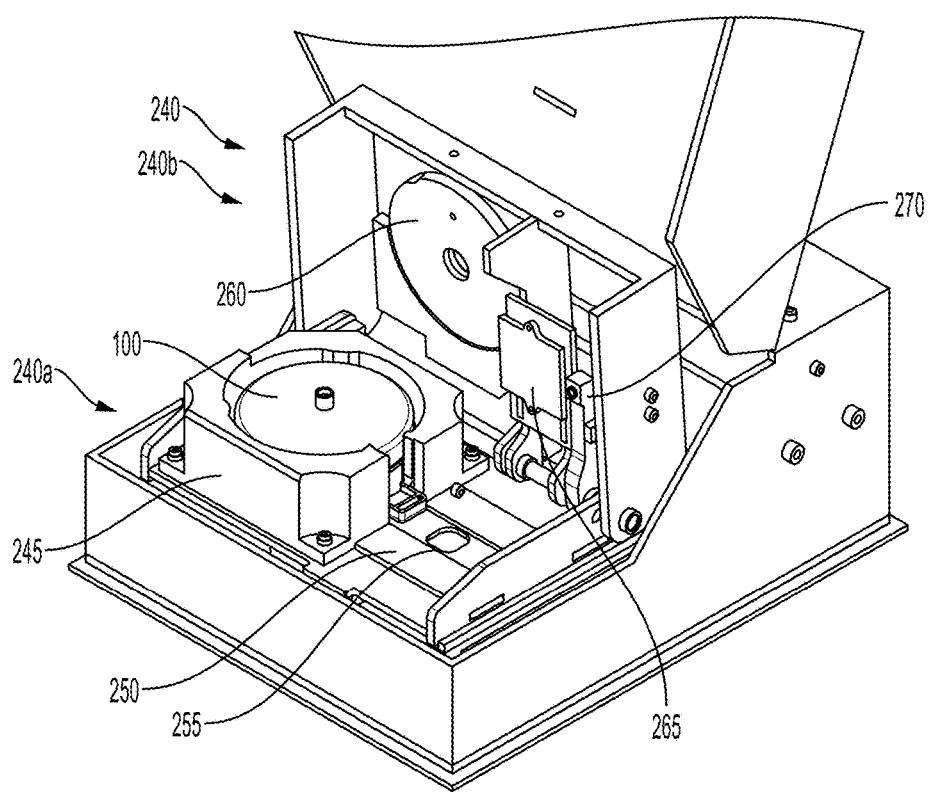
FIG. 2C shows a top perspective view of the diagnostic mechanism of the diagnostic platform of FIG. 2A.
Figure 2D:
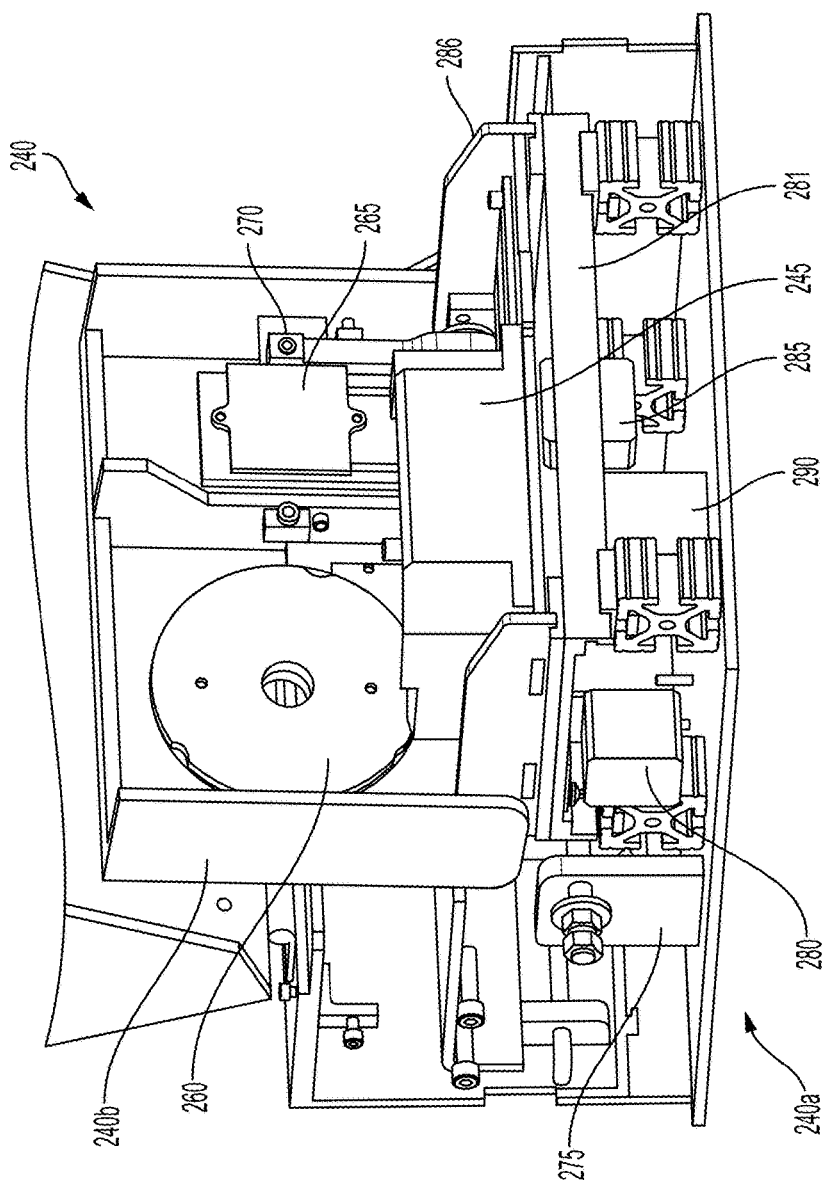
FIG. 2D shows a front perspective view of the diagnostic mechanism of the diagnostic platform of FIG. 2A with the front cover removed.
Figure 2E:
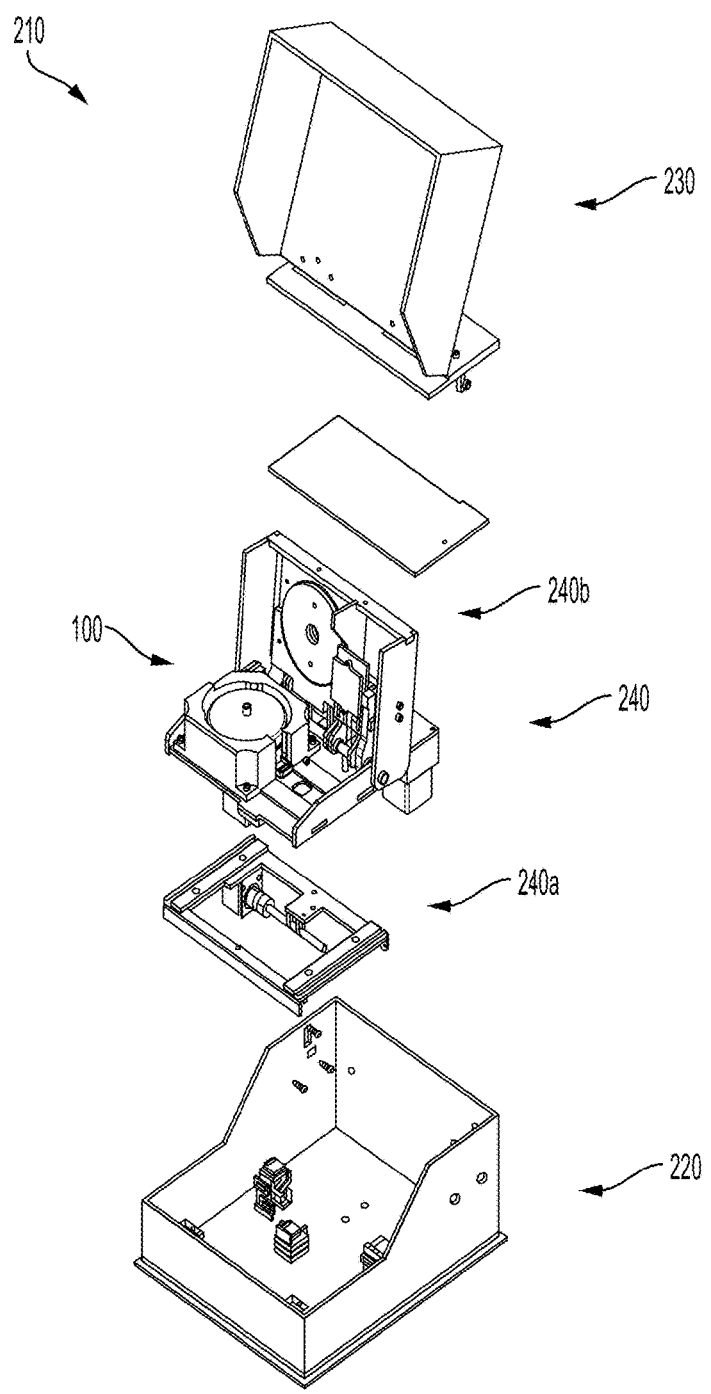
FIG. 2E shows an exploded view of the diagnostic platform of FIG. 2A.
Figure 2F:
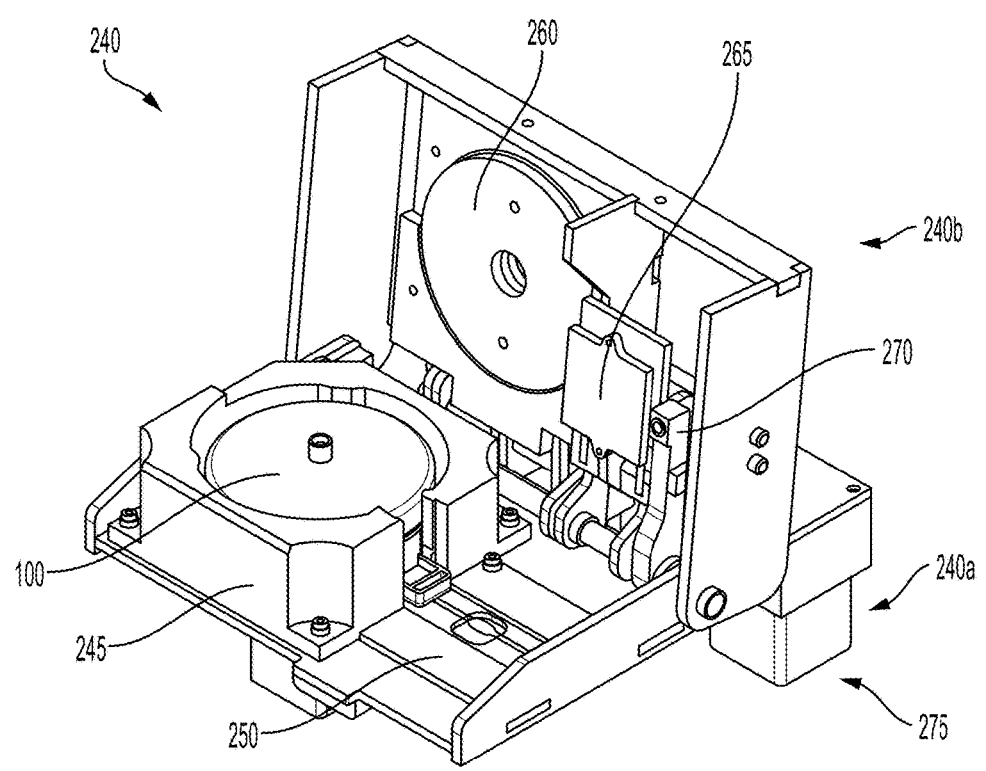
FIG. 2F shows a perspective view of the diagnostic mechanism of the diagnostic platform of FIG. 2A with the base and cover removed.
Figure 2G:
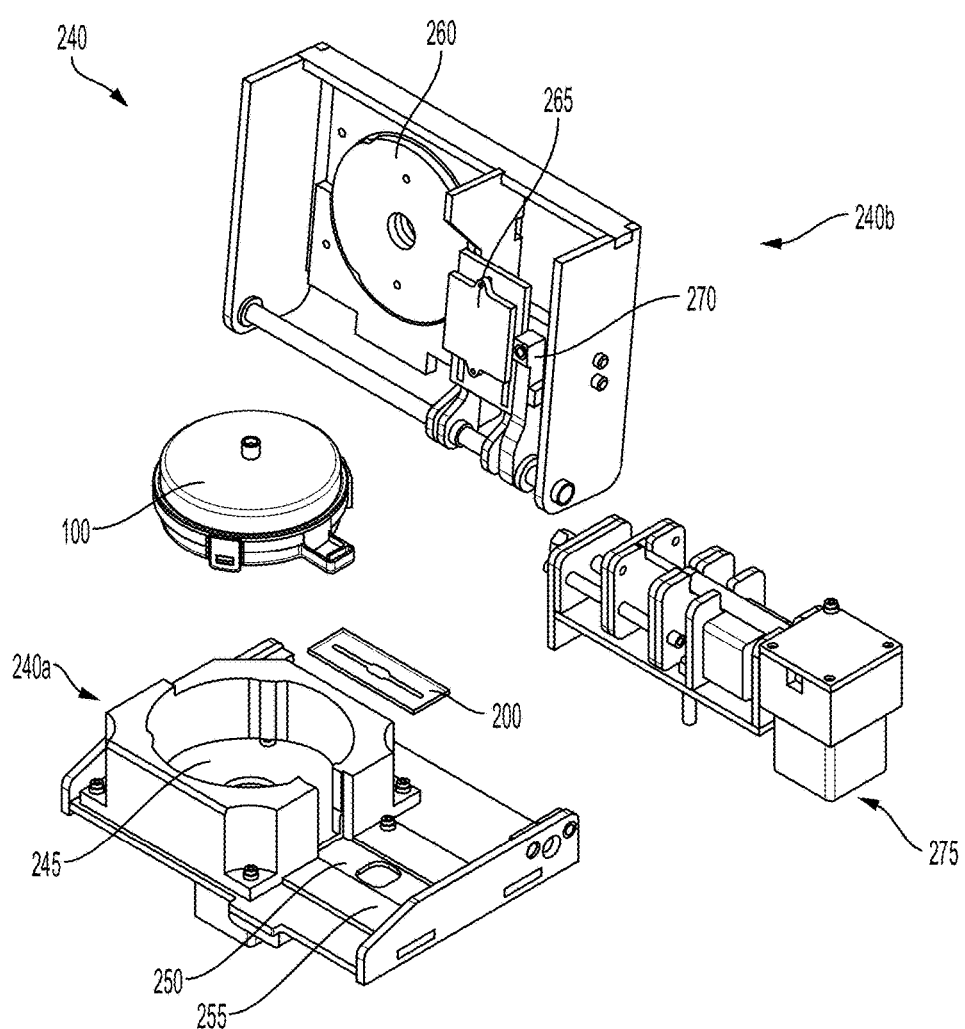
FIG. 2G shows an exploded view of the diagnostic mechanism of the diagnostic platform of FIG. 2A with the base and cover removed.
Figure 2H:
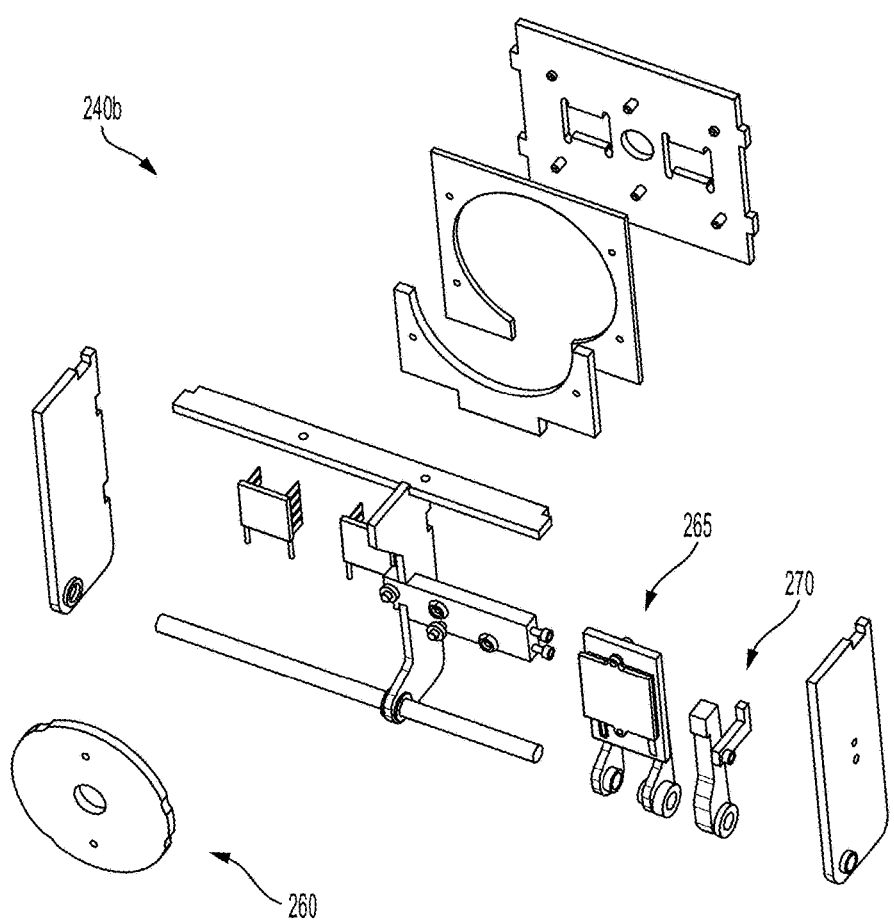
FIG. 2H shows an exploded view of the top portion of the diagnostic mechanism of the diagnostic platform of FIG. 2A with the base and cover removed.
Figure 21:
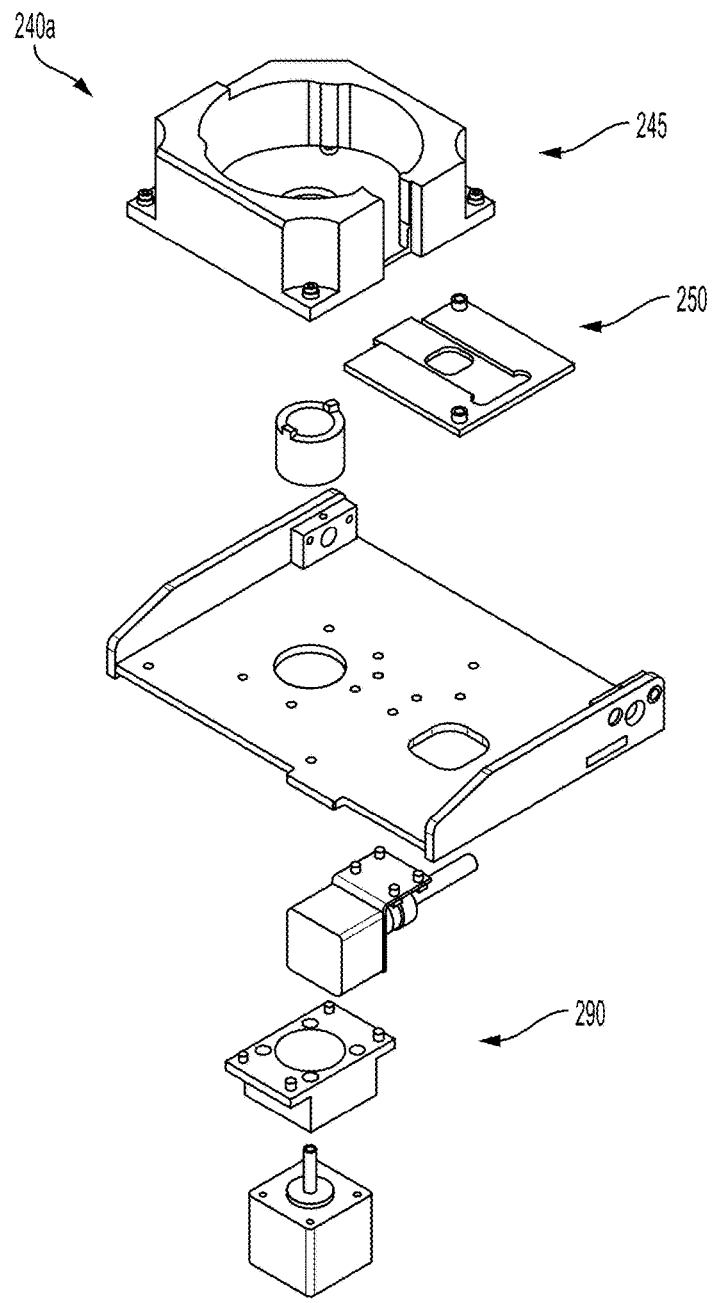

FIGS. 2C and 2D show magnified views of the diagnostic mechanism 240. FIG. 2E shows an exploded view of the diagnostic platform 210. FIGS. 2F and 2G show perspective and exploded views, respectively, of the diagnostic mechanism 240 of the diagnostic platform 210 with the outer shell 220 and cover 230 removed. The diagnostic mechanism 240 may have a bottom portion 240a and a top portion 240b. The bottom portion 240a and the top portion 240b may be pivotably coupled to one another. FIG. 2H shows an exploded view of the top portion 240b while FIG. 2I shows an exploded view of the bottom portion 240a.

The bottom portion 240a may comprise a cartridge receptacle 245 to receive the reagent storage and dispensing device 100, a flow cell receptacle 250 to receive the flow cell 200, and an aperture 255 through which the flow cell 200 may be imaged. An imaging source or optics may be a component of the diagnostic mechanism 240 or may be separate from the diagnostic mechanism 240 (for example, such that the imaging source and optics are fixtures while diagnostic platform 210 may be disposable.) The bottom portion 240a may further comprise a syringe or other pump 275 which may be in fluid communication with the port 112 of the storage and dispensing device 100. The syringe or other pump 275 may be actuated to urge and/or withdrawn reagent and/or sample from the device 100. The bottom portion 240a may further comprise an X-scanner motor 280, an X-slide 281, a Y-scanner motor 285, and/or a Y-slide 286 to move the storage and dispensing device 100, the flow cell 200, and the imaging aperture 255 in two dimensions relative to the external imaging source. The bottom portion 240a may further comprise an actuator 290 which may couple to the valve assembly 130 of the storage and dispensing device 100 to select a well 142 for dispensing of its contents.

The top portion 240b of the diagnostic mechanism 240 may comprise a heat sink 260 to couple to and passively cool the storage and dispensing device 100. The top portion 240b may also comprise a pad 265 which may contact the flow cell 200 to heat or cool the flow cell 200. The top portion 240b may also comprise an outlet line 270 which may couple to the flow cell channel 201 of the flow cell 200 to collect waste or other fluid out of the flow cell channel 201. The heat sink 260 may be made of copper, aluminum, or other highly heat conductive metals, allows, ceramics, or other materials.

Figure 3A:
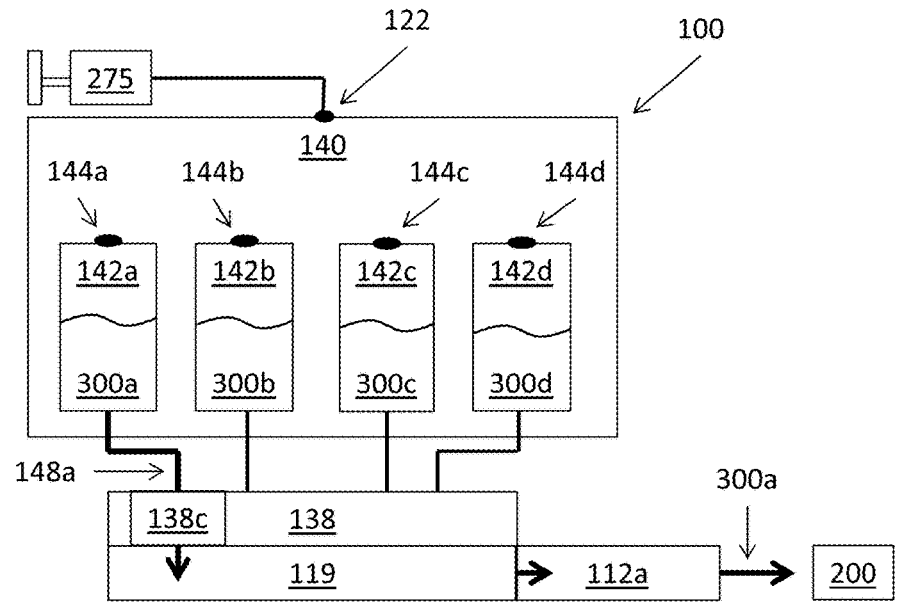
FIG. 3A shows a schematic of a first reagent well of an exemplary reagent storage and dispensing device being selected for fluid communication, in accordance with many embodiments.
Figure 3B:
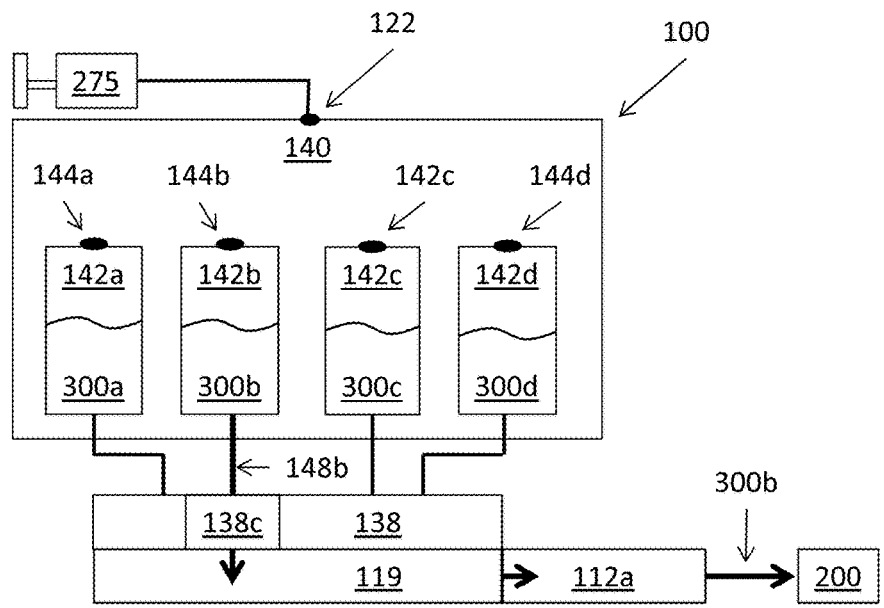
FIG. 3B shows a schematic of a second reagent well of the reagent storage and dispensing device of FIG. 3A being selected for fluid communication, in accordance with many embodiments.

FIGS. 3A and 3B show schematic diagrams of the storage and dispensing device 100 in use. A plurality of storage wells 142a, 142b, 142c, and 142d, storing fluids 300a, 300b, 300c, and 300d, respectively, may be housed within the internal volume 140. The storage wells 142a, 142b, 142c, and 142d may each have top ports 144a, 144b, 144c, and 144d, respectively, which allow the storage wells 142a, 142b, 142c, and 142d to be pressurized along with the internal volume 140. The pump 275 may introduce pressure into the internal volume 140 of the storage and dispensing device 100. The pump 275 may introduce a pre-determined, metered volume of fluid into the internal volume 140 through the inlet port 122 of the device 100, for example.

The fluid may be introduced at various flow rates and/or for various times as desired to affect an outflow of fluid from the dispensing device 100. The fluid from one or more of the storage wells 142a, 142b, 142c, or 142d may be provided from the device 100 at precise volumes and/or flow rates as desired. For example, the fluid may be introduced at a flow rate of at least 0.1 µL/s, 0.2 µL/s, 0.3 µL/s, 0.4 µL/s, 0.5 µL/s, 0.6 µL/s, 0.7 µL/s, 0.8 µL/s, 0.9 µL/s, 1.0 µL/s, 1.1 µL/s, 1.2 µL/s, 1.3 µL/s, 1.4 µL/s, 1.5 µL/s, 1.6 µL/s, 1.7 µL/s, 1.8 µL/s, 1.9 µL/s, 2.0 µL/s, 2.1 µL/s, 2.2 µL/s, 2.3 µL/s, 2.4 µL/s, 2.5 µL/s, 2.6 µL/s, 2.7 µL/s, 2.8 µL/s, 2.9 µL/s, 3.0 µL/s, 3.1 µL/s, 3.2 µL/s, 3.3 µL/s, 3.4 µL/s, 3.5 µL/s, 3.6 µL/s, 3.7 µL/s, 3.8 µL/s, 3.9 µL/s, or 4.0 µL/s. For example, the fluid may be introduced at a flow rate of at most 10 µL/s, 9.5 µL/s, 9.0 µL/s, 8.5 µL/s, 8.0 µL/s, 7.5 µL/s, 6.0 µL/s, 5.5 µL/s, 5.0 µL/s, 4.5 µL/s, 4.0 µL/s, 3.5 µL/s, 3.0 µL/s, 2.5 µL/s, 2.0 µL/s, 1.5 µL/s, or 1.0 µL/s/s. For example, the fluid may be introduced for a time of at least 0.1 s, 0.2 s, 0.3 s, 0.4 s, 0.5 s, 0.6 s, 0.7 s, 0.8 s, 0.9 s, 1.0 s, 1.5 s, 2.0 s, 2.5 s, 3.0 s, 3.5 s, 4.0 s, 4.5 s, 5.0 s, 5.5 s, 6.0 s, 6.5 s, 7.0 s, 7.5 s, 8.0 s, 8.5 s, 9.0 s, 9.5 s, or 10.0 s. For example, the fluid may be introduced for a time of at most 60 s, 55 s, 50 s, 45 s, 40 s, 35 s, 30 s, 25 s, 20 s, 15 s, 10 s, or 5 s. For example, the fluid may be introduced at a discrete volume of at least 0.1 µL, 0.2 µL, 0.3 µL, 0.4 µL, 0.5 µL, 0.6 µL, 0.7 µL, 0.8 µL, 0.9 µL, 1.0 µL, 1.5 µL, 2.0 µL, 2.5 µL, 3.0 µL, 3.5 µL, 4.5 µL, 5.0 µL, 5.5 µL, 6.0 µL, 6.5 µL, 7.0 µL, 7.5 µL, 8.0 µL, 8.5 µL, 9.5 µL, 10.0 µL, 11.0 µL, 12.0 µL, 13.0 µL, 14.0 µL, 15.0 µL, 16.0 µL, 17.0 µL, 18.0 µL, 19.0 µL, 20.0 µL, 25.0 µL, 30.0 µL, 35.0 µL, 40.0 µL, 45.0 µL, 50.0 µL, 55.0 µL, 60.0 µL, 65.0 µL, 70.0 µL, 75.0 µL, 80.0 µL, 85.0 µL, 90.0 µL, 95.0 µL, 100.0 µL, 150.0 µL, 200.0 µL, 250.0 µL, 300.0 µL, 350.0 µL, 400.0 µL, 450.0 µL, 500.0 µL, 550.0 µL, 600.0 µL, 650.0 µL, 700.0 µL, 750.0 µL, 800.0 µL, 850.0 µL, 900.0 µL, 950.0 µL, or 1.0 mL, 2.0 mL, 3.0 mL, 4.0 mL, 5.0 mL, 6.0 mL, 7.0 mL, 8.0 mL, 9.0 mL, or 10.0 mL. For example, the fluid may be introduced at a discrete volume of at most 10.0 mL, 9.0 mL, 8.0 mL, 7.0 mL, 6.0 mL, 5.0 mL, 4.0 mL, 3.0 mL, 2.0 mL, 1.0 mL, 0.9 mL, 0.8 mL, 0.7 mL, 0.6 mL, 0.5 mL, 0.4 mL, 0.3 mL, 0.2 mL, or 0.1 mL.

The top ports 144a, 144b, 144c, and 144d may also allow samples, reagents, buffers, and other fluids to be introduced into the storage wells 142a, 142b, 142c, and 144d, respectively. For example, a syringe needle or other tubing may be passed through the inlet port 122 and to one of the top ports 144a, 144b, 144c, and 144d to provide fluids to the storage wells 142a, 142b, 142c, and 142d. Fluid may be removed from the storage wells 142a, 142b, 142c, and 142d similarly. Alternatively or in combination, the storage and dispensing device 100 may be manufactured with the desired fluids already stored in one or more of the wells 142a, 142b, 142c, or 142d.

While the storage wells 142a, 142b, 142c, and 142d may each be pressurized along with the internal volume 140, only the storage well 142 selected for fluid dispensing may have the fluid therein egress from the device 100. To select an individual storage well for fluid egress, the dispensing piece 138 of the valve assembly 130 may be actuated so that the channel 138c of the dispensing piece 138 aligns with the individual outlet channel 148 of the selected storage well 142 and the outlet manifold 119. At the same time, the dispensing piece 138 may prevent or restrict fluid communication between the remaining individual outlet channels 148 of the unselected wells 142 and the outlet manifold 119. The dispensing piece 138 and/or valve assembly may include a marker to indicate which of the storage wells 142 is selected. Alternatively or in combination, the device 100 may be made of transparent materials in whole or in part so the user can see which storage well 142 has been selected. The dispensing piece 138 may be actuated to select the individual storage well 142 while the remainder of the device 100 remains stationary, reducing the number of moving parts and minimizing mechanical fatigue.

As shown in FIG. 3A, the channel 138c of the dispensing piece 138 may be aligned with the individual outlet channel 148a of the first storage well 142a. Pressurization of the internal volume 140 may pressurize the first storage well 142a and may cause the first fluid 300a within the first storage well 142a to egress from the first storage well 142a, through its individual outlet channel 148a, through the channel 138c, through the outlet manifold 119, out through the shared outlet channel 112a, and into the flow cell 200. Other devices instead of the flow cell 200 may receive the outflowing second fluid 300b as well. When the first storage well 142a is selected, the dispensing piece 138 may restrict or prevent fluid communication from the individual outlet channels 148 of the remaining storage wells 142b, 142c, and 142d to the outlet manifold 119.

Other storage wells may be selected for fluid dispensing. As shown in FIG. 3B, the dispensing piece 138 may be actuated so that the channel 138c is aligned with the individual outlet channel 148b of the second storage well 142b. Pressurization of the internal volume 140 may pressurize the second storage well 142b. When the second storage well 142b is selected, the dispensing piece 138 may restrict or prevent fluid communication from the individual outlet channels 148 of the remaining storage wells 142a, 142c, and 142d to the outlet manifold 119. On the other hand, the channel 138c may provide fluid communication between the individual outlet channel 148b of the second storage well 142b and the outlet manifold 119. Pressurization of the second storage well 142b may cause the second fluid 300b within the second storage well 142b to egress from the second storage well 142b, through its individual outlet channel 148b, through the channel 138c, through the outlet manifold 119, out through the shared outlet channel 112a, and into the flow cell 200. Other devices instead of the flow cell 200 may receive the outflowing second fluid 300b as well. The other storage wells 142c and 142d may likewise be selected to dispense fluids 300c and 300d therein, respectively.

Aspects of the present disclosure also include computer-based systems and computer-implemented methods for performing a fluid dispensing protocol for one or more of the device 100 and the diagnostic platform 210.

Figure 4:
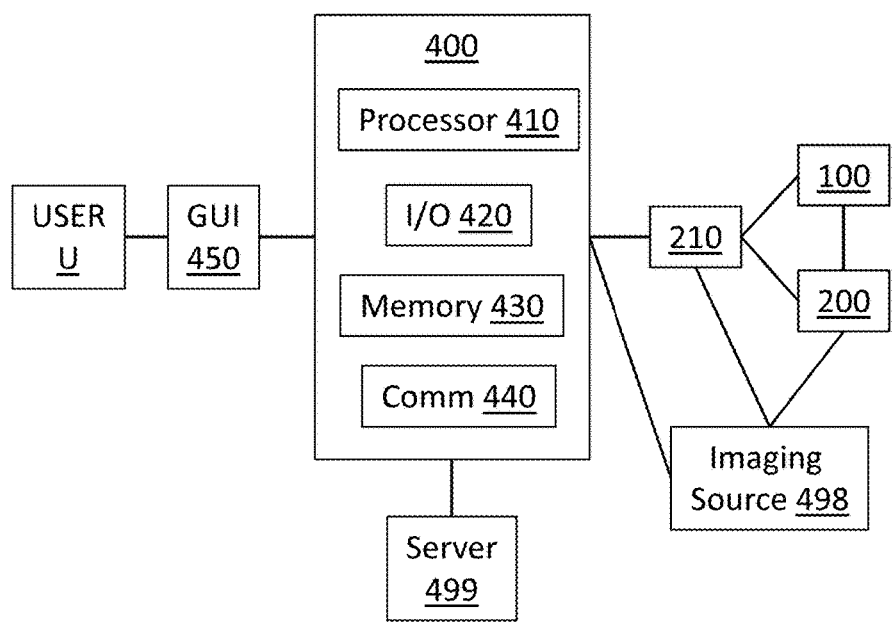
FIG. 4 shows a schematic of an exemplary computer-system for operating the device of FIG. 1A and/or the diagnostic platform of FIG. 2A.
Figure 5:
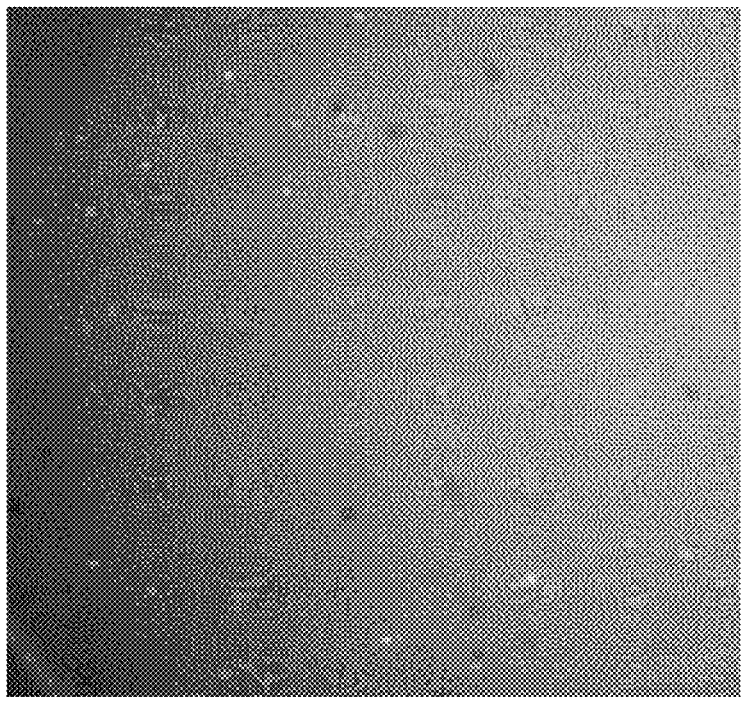
FIG. 5 shows an image of dyed clusters in a flow cell which had been used with the reagent storage and dispensing device of FIG. 1A to perform a biochemical reaction.

FIG. 4 shows an exemplary computer-system 400 for operating the storage and dispensing device 100 and/or the diagnostic platform 210. The computer system 400 may comprise a CPU or processor 410, an input/output system 420, a memory 430 (such as a ROM, RAM, Flash memory, hard disk drive, or the like), and a communications subsystem 440 (such as an Ethernet card, a WiFi card, a Bluetooth card, or the like). The user U may operate the computer system 400 through a graphical user interface 450 of the computer system 400. The graphical user interface 450 may be provided through a display coupled to the computer system 400, such as a touch screen display. The computer system 400 may be a mobile computing device (such as a laptop computer, tablet computer, a smart phone, a wearable computer, or the like), a personal computer, a workstation, or a dedicated computing platform. The memory 430 may have stored thereon software including one or more protocols for operating one or more of the storage and dispensing device 100, the diagnostic platform 210, or an imaging source 498. The imaging source 498 may comprise a component of the computer system 400 or may comprise a stand-alone device. The image source 498 may be comprise a conventional light microscope, a digital microscope, a confocal microscope, a line confocal microscope, a scanning microscope, a fluorescence microscope, a laser scanning microscope, a multi-photon microscope, an epifluorescence microscope, combinations thereof, or the like.

One or more of the imaging source 498 or diagnostic platform 210 may be in communication with the computer system 400 to receive instructions therefrom to operate the imaging source or to operate the device 100 coupled to the diagnostic platform 210, respectively. The computer system 400 may instruct the imaging source 498 and diagnostic platform 210 to perform a dispensing protocol for a sequential reaction as described herein and to image the reaction as it occurs in the flow cell 200 coupled to the device 100. The computer system 400 may one or more of receive the images of the sequential reaction, store the images on the memory 430, or communicate the images to a remote server 499, which may include cloud-based storage, for example. The reagent dispensing and sequential reaction protocol may be pre-programmed in the memory 430 of the computing system 400. Alternatively or in combination, the user U may enter or modify a reagent dispensing and sequential reaction protocol into the computing system 400.

The reagent dispensing and sequential reaction protocol may be any number of protocols. Often, the protocol performed may depend on the contents of the device 100. For example, a first device 100 having a first set of reagents and sample(s) stored therein may be labeled as appropriate to perform a first protocol. The diagnostic platform 210 may read the label and communicate to the system 400 to operate the imaging source 498 and the diagnostic platform 210 to perform a first type of sequential reaction and imaging protocol. A second device 100 having a second set of reagents and sample(s) stored thereon different from the first set may be labeled as appropriate to perform a second protocol different from the first protocol. The diagnostic platform 210 may read the label and communicate to the system 400 to operate the imaging source 498 and the diagnostic platform 210 to perform a second type of sequential reaction and imaging protocol different from the first type. The labelling may comprise a bar code, a QR code, or the like. Alternatively or in combination, the user U may read the labelling on the device 100 and manually operate the computer system 400 to perform the appropriate protocol.

EXPERIMENTAL

Tests were performed using the storage and dispensing device 100. The device 100, along with the flow cell 200 attached thereto as described above, was used to perform a biochemical reaction.

Individual storage wells 142 of the device 100 were used to store one or more of formamide, a buffer mix, a DNA polymerase enzyme mix, or a dye (for example, a Cy3 dye mix). The buffer mix was stored in a first well, the DNA polymerase enzyme mix was stored in a second well, the dye was stored in a third well, and the sample was stored in a fourth well. These reagents were sequentially dispensed into the flow cell 200 to complete a DNA "cluster generation" process to prepare the flow cell 200 for shotgun sequencing by synthesis as known in the art. The reagents were sequentially introduced into the flow cell 200 for amplification in a first step, the reagents were given time (for example, 60 seconds) to react with one another in a second step, and the first and second steps were repeated multiple times. The valve assembly 130 was sequentially rotated to select individual storage wells 142 for egress of the stored fluid. Precise, predetermined volumes of air were introduced sequentially into the internal volume 140 to pressurize the internal volume and cause the selected fluid to egress from its storage well and the shared outlet channel 112. The volumes of fluid introduced into the internal volume were introduced at a predetermined flow rate to cause the selected fluid to egress with a predetermined and desired flow rate. The volumes of fluid introduced into the internal volume were introduced with a syringe pump 275 as described above.

The flow cell 200 was imaged as the sequential reactions take place. Each reagent was dispensed into the flow cell 200 at various flows rate, for various times, and at various volumes. These sequential reactions generated clusters. The resulting clusters were tagged with a Cy3 dye mix and appear as light spots under a fluorescence microscope as shown in FIG. 4. The image shown in FIG. 4 was taken after 33 sequential amplification reactions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for the storage and dispensing of one or more reagents or fluids, the apparatus comprising:
   a housing enclosing an internal volume and comprising an outlet channel and an inlet port configured to allow the internal volume to be pressurized;
   a plurality of storage wells disposed within the internal volume of the housing, the plurality of storage wells being selectively in fluid communication with the outlet channel and in fluid communication with the internal volume; and
   a valve coupled to the housing, the valve being rotatable to select an individual storage well to be in fluid communication with the outlet channel while preventing the remaining storage wells from being in fluid communication with the outlet channel,
   wherein pressurizing the internal volume of the housing causes fluid to be drawn into or egress from the selected individual storage well.

2. The apparatus of claim 1, wherein pressurizing the internal volume of the housing comprises introducing one or more of negative pressure or positive pressure to the internal volume.

3. The apparatus of claim 2, wherein the introduction of positive pressure into the internal volume causes a fluid stored in the selected individual storage well of the plurality of storage wells to egress through the outlet channel.

4. The apparatus of claim 2, wherein the introduction of negative pressure into the internal volume causes a fluid present in the outlet channel to be drawn into the selected individual storage well of the plurality of storage wells.

5. The apparatus of claim 2, wherein one or more storage wells of the plurality of storage wells comprises an open port to balance pressure between the internal volume and a storage volume of the one or more storage wells.

6. The apparatus of claim 1, wherein the housing comprises a base assembly, wherein the base assembly comprises a base coupled to the plurality of storage wells and a cap coupled to the base.

7. The apparatus of claim 6, wherein one or more of the cap or the base comprises a plurality of fluid transfer channels open to the plurality of storage wells.

8. The apparatus of claim 7, wherein the plurality of fluid transfer channels are coupled to the valve to allow the plurality of storage wells to selectively be in fluid communication with the outlet channel.

9. The apparatus of claim 7, wherein one or more of the cap or the base comprises an outlet manifold in fluid communication with the outlet channel.

10. The apparatus of claim 9, wherein the valve comprises a valve channel for allowing fluid communication between the outlet manifold and a selected fluid transfer channel of the plurality of fluid transfer channels.

11. The apparatus of claim 10, wherein at least a portion of the valve is configured to be actuated to place the valve channel in fluid communication between the outlet manifold and the selected fluid transfer channel.

12. The apparatus of claim 11, wherein when the individual storage well is selected, the valve is in fluid communication between the outlet manifold and a fluid transfer channel in fluid communication with the selected individual storage well.

13. The apparatus of claim 12, wherein the valve is rotatable to deselect the individual storage well such that the valve channel is no longer in fluid communication between the outlet manifold and the fluid transfer channel in fluid communication with the deselected individual storage well.

14. The apparatus of claim 1, wherein when the valve is rotated to select the individual storage well, the plurality of storage wells and the outlet channel remain stationary.

15. A system for imaging a flow cell, the system comprising:
   the apparatus for the storage and dispensing of one or more reagents or fluids of claim 1;
   a flow cell coupled to the outlet channel of the apparatus;
   an imaging source coupled to the flow cell to image the flow cell;
   a pressure source coupled to the inlet port of the housing of the apparatus to pressurize the internal volume of the housing;
   a waste storage chamber coupled to the flow cell; and
   an actuator for rotating the valve to select the individual storage well of the apparatus.

16. A method for dispensing one or more reagents, the method comprising:
   actuating a valve of a storage chamber to select a first fluid for dispensing, the first fluid being stored in a first storage well enclosed in the storage chamber, wherein selecting the first fluid for dispensing aligns a valve channel of the valve with a first transfer channel of the first storage well with an outlet manifold of the storage chamber to allow fluid communication therebetween;
   pressurizing an internal volume of the storage chamber to pressurize a first storage volume of the first storage well and cause the first fluid to egress from the first storage well and through the first transfer channel, valve channel, and outlet manifold; and
   actuating the valve to select a second fluid for dispensing, the second fluid being stored in a second storage well enclosed in the storage chamber, wherein selecting the second fluid for dispensing positions the valve channel out of alignment with the first transfer channel and the outlet manifold such that the first fluid is prevented from being dispensed from the first storage well.

17. The method of claim 16, wherein selecting the second fluid for dispensing aligns the valve channel with a second transfer channel of the second storage well with the outlet manifold to allow fluid communication therebetween.

18. The method of claim 16, wherein pressurizing the internal volume pressurizes storage volumes of a plurality of storage wells of the reagent storage chamber.

19. The method of claim 18, wherein pressurizing the plurality of storage wells causes only the first fluid to egress from the first storage well while fluids in the remaining storage wells do not egress therefrom.

20. The method of claim 16, wherein the first and second storage wells remain stationary while the valve is actuated to select the first or second fluid for dispensing.

* * * * *